United States Patent
Dhas

[19]

[11] Patent Number: 5,772,608
[45] Date of Patent: Jun. 30, 1998

[54] SYSTEM FOR SAMPLING ARTERIAL BLOOD FROM A PATIENT

[75] Inventor: V. Varaprabhu Dhas, Dewitt, N.Y.

[73] Assignee: The Research Foundation of State University of New York, Albany, N.Y.

[21] Appl. No.: 365,307

[22] Filed: Dec. 28, 1994

[51] Int. Cl.$^6$ .................................................. A61B 5/00
[52] U.S. Cl. ........................................ 600/578; 600/579
[58] Field of Search ................................. 128/764, 763, 128/762, 635, 771, 760.1; 604/49, 184, 183, 319

[56] References Cited

U.S. PATENT DOCUMENTS

| | | | |
|---|---|---|---|
| 4,838,855 | 6/1989 | Lynn | 604/49 |
| 5,084,034 | 1/1992 | Zanotti | 604/319 |

OTHER PUBLICATIONS

V.A.M.P.™ System by Baxter Healthcare Corporation (Santa Ana, CA) (May 1991).
Safedraw™ System by Viggo–Spectramed, a BOC Health Care Company (Oxnard, CA) (1990).
Secure™ System by Medex Inc. (Hilliard, OH) (Jul. 1992).

*Primary Examiner*—Max Hindenburg
*Assistant Examiner*—Pamela Wingood
*Attorney, Agent, or Firm*—Jaeckle Fleischmann & Mugel, LLP

[57] ABSTRACT

The present invention relates to a system for sampling arterial blood from a patient. The system includes a reservoir suitable for containing fluid connected to a first end of a conduit. A connector suitable for connection to an artery of a patient is attached to the second end of the conduit. The system for sampling also includes a fluid displacement system which has a second conduit having first and second ends. A controller is positioned in the second conduit to permit fluid flow through the second conduit. The displacement system also includes a junction at the first end of the second conduit where the second conduit connects to the first conduit. A flow regulator is operative in a first mode to convey fluid to a patient through the first conduit from the reservoir and operative in a second mode to remove blood from a patient and convey it in the first conduit to a limit location. The limit location is positioned between the second end of the first conduit and the junction so that removal of blood in the second mode causes fluid previously in the first conduit to move into the fluid displacement system. A sampling station is positioned in the first conduit between the limit location and the second end of the first conduit. The present invention is further directed to a method of utilizing this system as well as to the displacement system alone.

14 Claims, 2 Drawing Sheets

SYSTEM FOR SAMPLING ARTERIAL BLOOD FROM A PATIENT

FIELD OF THE INVENTION

The invention relates to a system for sampling arterial blood from a patient.

BACKGROUND OF THE INVENTION

In recent years, obtaining blood samples from arterial lines of patients has raised concerns about patient blood loss, potential patient infection, and exposure of healthcare professionals to pathogens such as HIV and hepatitis. Excessive blood loss from repeated sampling can threaten patient safety and necessitate a transfusion. Blood contamination can increase the threat of Nosocomial infection, which can add up to two weeks to the stay of an intensive care unit patient. Accidental exposure of a healthcare professional to HIV or hepatitis can result in illness or even death.

In response to these concerns, various blood sampling systems have been developed. These sampling systems have not, however, been entirely satisfactory. Blood sampling systems currently being used include the V.A.M.P.™ system by Baxter Healthcare Corporation (Santa Ana, Calif.), the Safedraw™ system by Viggo-Spectramed, a BOC Health Care Company (Oxnard, Calif.), and the SECURE™ system by Medex Inc. (Hilliard, Ohio).

The V.A.M.P.™ blood sampling system includes a single arterial line which may be connected to a patient, and a sampling site configured to receive a needleless cannula. A shut-off is positioned downstream of the sampling site, with a reservoir yet further downstream. Samples are taken by connecting the arterial line to the patient, allowing blood to enter the single arterial line, and removing blood from the sampling site. To return residual blood in the arterial line to the patient, the reservoir is filled with a clearing solution, the shut-off valve is opened, and the reservoir is emptied to displace blood from the line. Potential problems encountered with this system include: (1) potential alteration of pressure transmission due to the presence of a tortuous fluid path; (2) potential sample dilution due to the lack of a means to stop infusate flow to the sampling port; (3) potential blood cell destruction due to the pressure required to return infusate and blood to the patient; and (4) potential contamination and blood leakage due to multiple punctures of the latex disc used at the sampling site.

The Safedraw™ blood sampling system is also a single line system. Here, blood is drawn from the line by retracting a permanently mounted syringe. The sample is then taken with a different syringe. This system is integrated with a blood pressure monitoring transducer. During sampling, flow to the transducer is shut-off. Potential problems resulting from use of this system include: (1) the above-noted difficulties of pressure transmission alteration, diminution in sample quality, and increased exposure risk due to the use of silicon sampling septums; (2) potential blood cell destruction due to the tortuous fluid path through the narrow lumen of the sampling port and the pressure required to draw back the reflux volume; and (3) potential inadequate sample volume due to limitations imposed by the size of the permanently mounted syringe.

The Medex SECURE™ blood sampling system has two lines—an arterial line suitable for connection to the patient and a displacement line extending from the arterial line. In the Medex system, a fluid controlling valve is positioned in the arterial line and must be held in an operative position by healthcare personnel in order for liquid to flow through the arterial line. This precludes a saline drip from being maintained through the arterial line in order to keep the patient's catheter open. Additionally, pressure resulting from the fluid controlling valve can damage cells being sampled and, as a result, alter the sample's sodium/potassium electrolyte balance. Further possible problems encountered with the Medex system include: (1) potential contamination of blood due to ref lux infusate passing through a blood pressure transducer; (2) potential alteration of pressure transmission due to use of a latex sampling port; (3) potential sample dilution due to the lack of a means to stop infusate flow to the sampling port; and (4) potential contamination and blood leakage due to multiple punctures of the sampling port.

The present invention is directed to overcoming these deficiencies.

SUMMARY OF THE INVENTION

The present invention is a system for sampling arterial blood from a patient. The system includes a reservoir suitable for containing fluid connected to a first end of a conduit. A connector suitable for connection to an artery of a patient is attached to the second end of the conduit. The system for sampling also includes a fluid displacement system which has a second conduit having first and second ends. A controller is positioned in the second conduit to permit fluid flow through the second conduit. The displacement system also includes a junction at the first end of the second conduit where the second conduit connects to the first conduit. A flow regulator is operative in a first mode to convey fluid to a patient through the first conduit from the reservoir and operative in a second mode to remove blood from a patient and convey it in the first conduit to a limit location. The limit location is positioned between the second end of the first conduit and the junction so that removal of blood in the second mode causes fluid previously in the first conduit to move into the fluid displacement system. A sampling station is positioned in the first conduit between the limit location and the second end of the first conduit.

This system is utilized to carry out a method for sampling arterial blood from a patient. In this method, the flow regulator is operated in the second mode to convey blood from the patient through the first conduit to the limit location. This displaces fluid previously in the first conduit into the fluid displacement system. A blood specimen is then collected from the sampling station. After collection of the blood specimen, the flow regulation system is operated in the first mode to convey fluid from the reservoir to the patient through the first conduit. As a result, blood removed from the patient during operation of the flow regulation system in the second mode is reinfused into the patient.

A subcombination of the system for sampling arterial blood relates to a minimizer system which includes a fluid displacement conduit having a first end and a second end. A receptacle suitable for containing fluid is connected to the first end of the fluid displacement conduit. A flow regulator is connected to the second end of the fluid displacement conduit and is suitable to be joined to a fluid flow line connected to the artery of a patient. The flow regulator is operative in a first mode to convey fluid in the fluid flow line through the flow regulator and to the patient. The flow regulator is operative in a second mode to remove blood from the patient and convey it through the fluid flow line, causing fluid previously in the fluid flow line to move into the fluid displacement conduit. A valve controls fluid flow into the fluid displacement conduit.

The instant invention confers many benefits over prior art arterial blood sampling systems. These advantages include:

decreased exposure risk for healthcare professionals; elimination of the need to discard patient blood; and decreased incidence of catheter-related sepsis. In addition, the present invention does not dilute the sample, provides an adequate blood sample volume, and reduces the potential for contamination and blood leakage.

DETAILED DESCRIPTION OF THE DRAWINGS AND THE INVENTION

Figure 1:
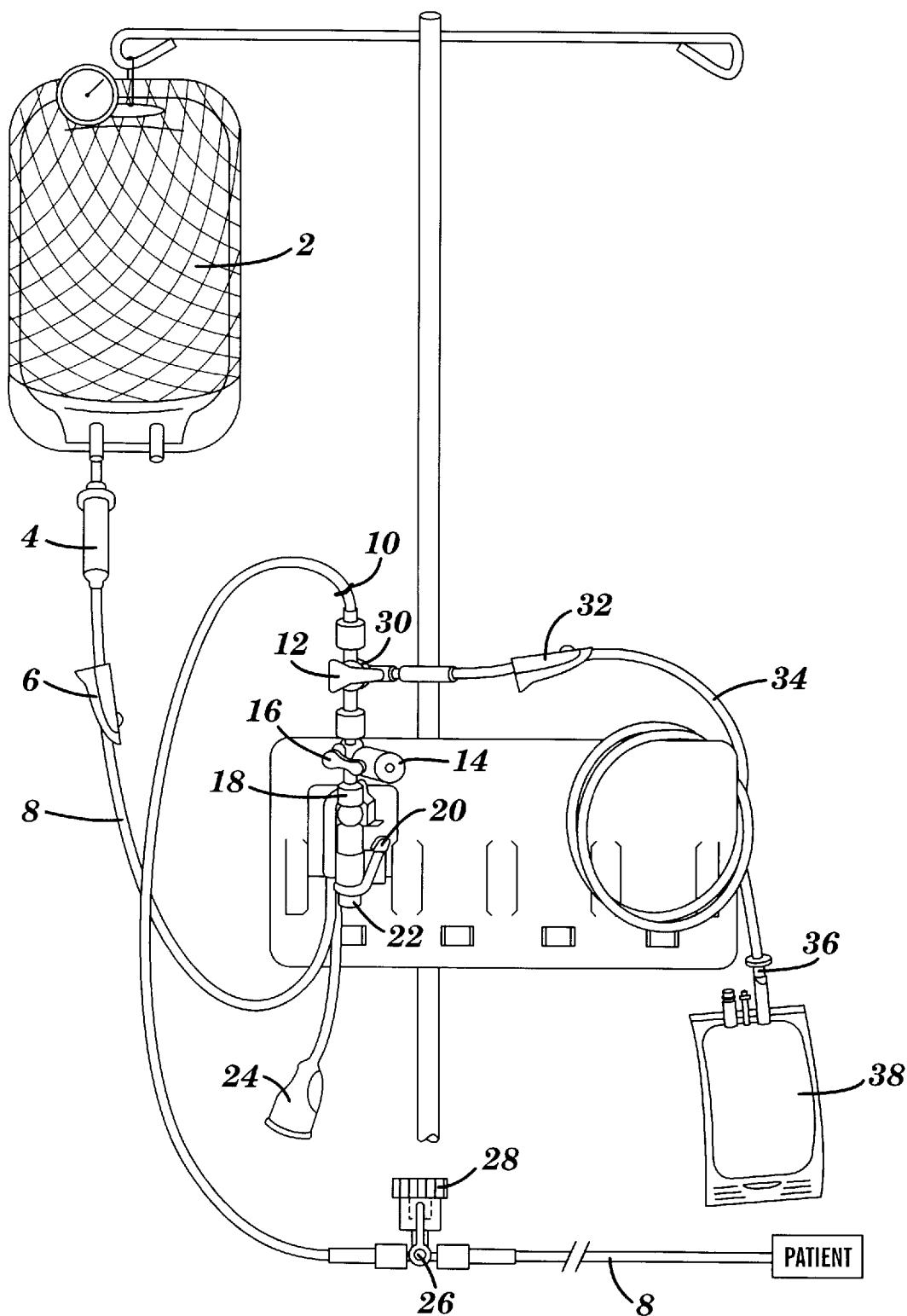
FIG. 1 is a schematic view of a system for sampling arterial blood from a patient in accordance with the present invention.

FIG. 1 is a schematic view of a system for sampling arterial blood from a patient in accordance with the present invention. The system includes reservoir 2 containing saline (or another suitable liquid for infusion into a patient) which is connected by connector 4 to conduit 8. Fluid flow from reservoir 2 may be halted with valve 6 (known as a roller clamp). Conduit 8 is joined to valve 12 at junction 30 immediately after limit location 10.

Calibration port 14 having valve 16 is positioned in conduit 8 proximate to valve 12. Positioned within conduit 8 is transducer connection 18 which is coupled to transducer housing 22 in order to measure the patient's blood pressure. This information is provided to a conventional electronic digital read-out (not shown) via connector 24. Thus, the transducer measures the pressure of any liquid passing through conduit connection 18. Suitable transducers are well known in the art with examples being found in the Safedraw™, SECURE™, and V.A.M.P.™ systems described above. The flow rate of liquid in conduit 8 from reservoir 2 can be controlled at two levels by lever 20. At its normally-maintained orientation, lever 20 partially blocks fluid flow in conduit 8 to permit a low flow rate from reservoir 2 to the patient. This is useful for normal dripping of saline to the patient. When lever 20 is held in a depressed position by the hospital operator, lever 20 no longer even partially blocks conduit 8 and, instead, permits a high fluid flow rate for as long as the operator depresses lever 20. This position of lever 20 facilitates flushing the system as described below.

Sampling station 28 is connected to conduit 8 and is located between the patient and limit location 10. Operation of sampling station 28 is controlled by valve 26 which is operable in 3 positions. In a first position, when a sample is not being withdrawn at sample station 28, valve 26 allows fluid to flow past sampling station 28 through conduit 8. As a result, fluid can flow between reservoir 2 and the patient. However, when a blood sample is to be taken, valve 26 is moved to a second position where fluid flow in conduit 8 between reservoir 2 and the patient is halted, and a blood sample can be withdrawn from the portion of conduit 8 between sampling station 28 and the patient. Thus, valve 26 permits sampling station 28 to be opened so that a blood sample can be withdrawn. In a third position, valve 26 prevents fluid flow between reservoir 2 and the patient through conduit 8 but allows liquid from reservoir 2 to be discharged at sampling station 28 in order to flush the system. This position prevents liquid from entering or leaving the patient through conduit 8.

Conduit 8 is connected to the patient (not shown) by an intravenous needle or other catherization implement (not shown). The flow of saline or other liquid from reservoir 2 through conduit 8 to the patient keeps access to the patient's artery open so that fluid can be added or removed from the patient.

The system also includes a minimizer system formed by conduit 34 which is connected by connector 36 to receptacle 38. Fluid flow through conduit 34 may be halted with either valve 32 (known as a roller clamp) or valve 12. Valve 12 is in the form of a 2-way stopcock, which, in one position, permits fluid flow through conduit 8 between reservoir 2 and the patient, while fluid flow from conduit 8 to conduit 34 is prevented. In the other position, valve 12 permits fluid flow between conduits 8 and 34 but prevents fluid flow via conduit 8 from reservoir 2 to the patient. Conduit 8 is connected with conduit 34 at junction 30.

The interplay of valve 32, valve 12, and valve 26 regulates fluid flow through conduits 8 and 34. In a first mode, valve 26 is positioned to permit flow past sampling station 28, valve 32 is closed, and valve 12 is open to allow flow through conduit 8 while closing off conduit 34. This mode may be used to maintain a saline drip to the patient from reservoir 2.

In a second mode, valve 26 is positioned to permit flow past sampling station 28, valve 32 is open, and valve 12 is off to conduit 8 (thereby preventing fluid flow from reservoir 2 to the patient) while opening fluid communication between conduit 8 and conduit 34. This mode may be used to draw blood from the patient in order to take blood samples. Here, pressure generated by the patient's heart causes blood to flow from the patient in conduit 8. Once the blood has reached limit location 10, valve 26 is actuated to open sampling station 28 for removal of a blood sample. In this position, valve 26 prevents fluid flow in conduit 8 past sampling station 28. After the blood sample is taken, valve 26 is actuated to the position that permits fluid flow in conduit 8 past sampling station 28, and prevents sample removal. The blood remaining in conduit 8 can then be reinfused into the patient by operating the system in the previously-described first mode.

In a third mode, any residual blood in the space between valve 26 and the sample removal point in sampling station 28 is flushed from the system. To do this, valve 26 is positioned to prevent fluid flow past sampling station 28 to the patient, while allowing removal of liquid at sampling station 28. Valve 32 is off, and valve 12 is open to permit fluid flow between reservoir 2 and sampling station 28 through conduit 8, while fluid communication between conduit 8 and conduit 34 is prevented. Sampling station 28 is cleaned in this mode by permitting saline to flow from reservoir 2 into conduit 8 and to be discharged at sampling station 28 into a closed container (not shown). In the first mode, lever 20 is not pressed by the operator and therefore partially blocks liquid flow from reservoir 2 to the patient. In this orientation, lever 20 allows a low flow rate (e.g. 3 cc/hr) to pass from reservoir 2 to the patient. In the third mode, lever 20 is pressed by the operator so that it no longer even partially blocks the flow of fluid in conduit 8 from reservoir 2. As a result, the liquid flows at a higher flow rate (e.g., 5–6 cc/hr) to flush debris from the system through sampling station 28 into a closed container (not shown).

Figure 2:
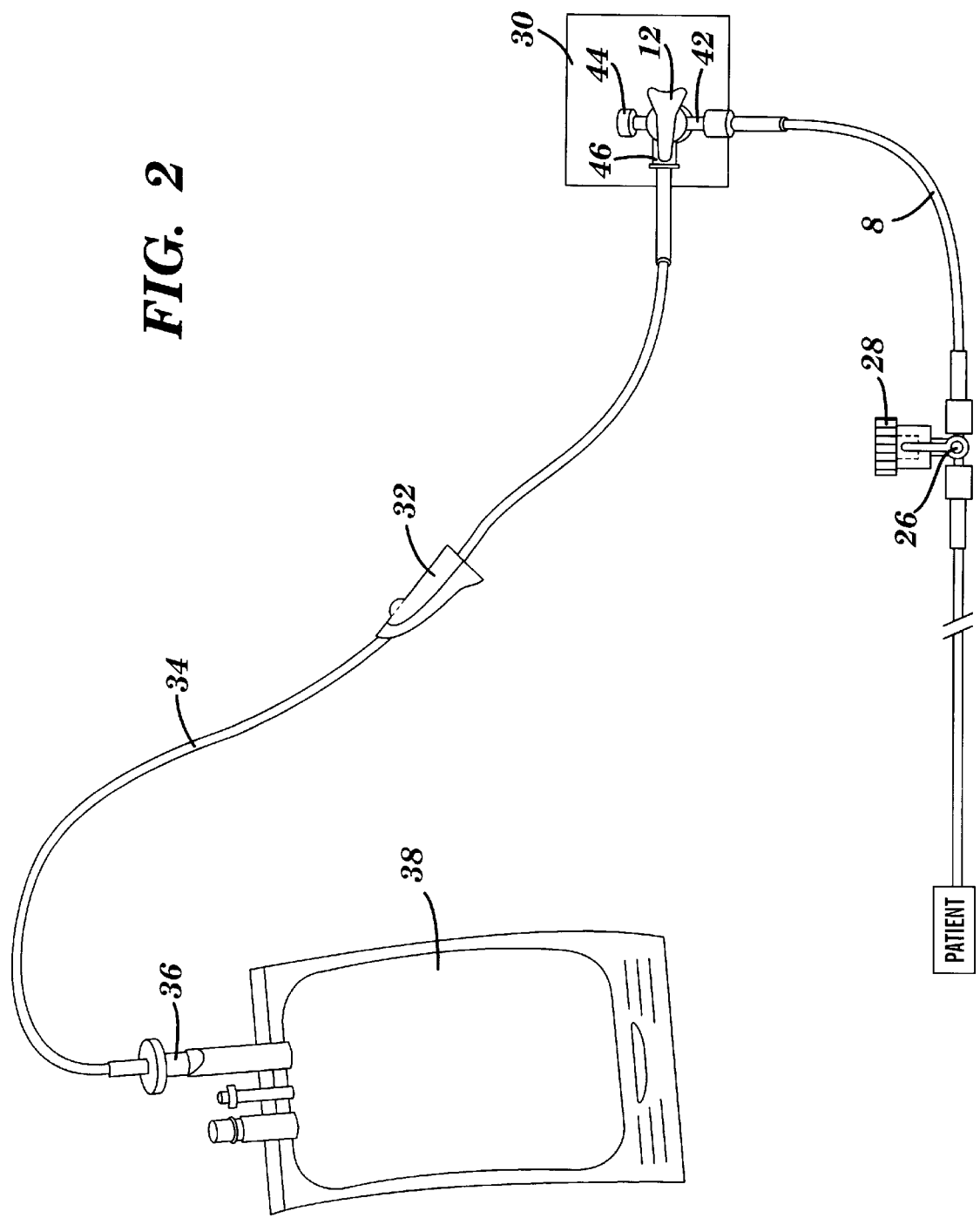
FIG. 2 is a schematic view of a minimizer system which is a component of FIG. 1.

FIG. 2 is a schematic view of the minimizer system component used in the system of FIG. 1. The system of FIG. 2 includes conduit 34 connected by connector 36 to receptacle 38, and connected by connector 46 to junction 30. Fluid flow through conduit 34 may be halted with valve 32. Conduit 8 is connected to conduit 34 by connector 42 at junction 30. As also depicted in FIG. 1, sampling station 28 is located in conduit 8 between junction 30 and the connection to the patient (not shown). As noted above, fluid flow through conduit 8 between reservoir 2 and the patient can be halted at sampling station 28 through the use of lever 26 in order to remove a blood sample. As also discussed with respect to FIG. 1, valve 12 is operable in two positions and can serve to block fluid flow through conduit 8 between reservoir 2 and the patient or to block fluid flow from conduit 8 into conduit 34.

In operation, the sampling system of the present invention can normally be used in the first mode to provide saline or other fluid in reservoir 2 to a patient through conduit 8 in order to maintain access to the patient's artery. In this mode, saline or other fluid in reservoir 2 passes through connector 4, valve 6, valve 16, valve 12, and valve 26 in conduit 8. Thus, in the first mode, saline is conveyed through the system of the present invention from reservoir 2 to the patient. In this mode, valve 6 is open, while valves 6 and 26 are positioned to permit fluid flow between reservoir 2 and the patient. In addition, valve 12 is open for such passage of liquid through conduit 8 but not for passage of liquid from conduit 8 into conduit 34.

When drawing a blood sample from the patient, the sampling system of the present invention must be operated in the second mode. This involves actuating lever 12 to prevent fluid flow through conduit 8 between reservoir 2 and the patient. In this position, valve 12 opens fluid communication between conduit 8 and conduit 34. As a result, the patient's heart pumps blood from the patient's artery into conduit 8, past valve 26, and up to limit location 10. This flow of blood into the sampling system of the present invention displaces saline previously in conduit 8 between the patient and limit location 10 past valve 12, valve 32, conduit 34, and connector 36 into receptacle 38. Once the blood reaches limit location 10, flow of liquid from the patient is stopped by closing valve 32. A sample of blood can then be withdrawn from sampling station 28 by moving valve 26 to the position providing fluid communication between sample station 28 and the portion of conduit 8 leading to this patient. This position, in turn, prevents the flow of fluid from reservoir 2 through conduit 8 past sampling station 28.

Once the blood sample is taken, the sampling system of the present invention can be operated again in the first mode by moving valve 12 to the position which allows liquid in reservoir 2 to pass through conduit 8 to the patient, while closing off fluid communication between conduit 8 and conduit 34. In addition, valve 26 is moved to a position which allows liquid to flow through conduit 8 from reservoir 2 to the patient past sampling station 28. This causes blood in conduit 8 between limit location 10 and the patient to be reinfused into the patient. Since valve 32 is operated in the second mode to prevent blood from passing limit location 10, all blood not removed as a sample at sampling station 28 can be reinfused into the patient.

Next, any residual blood at sampling station 28 can be removed from the system in the third mode. In this mode, valve 32 is turned off, while valve 12 is in the position allowing fluid to flow from reservoir 2 to the patient through conduit 8, while communication between conduits 8 and 34 is prevented. Meanwhile, valve 26 is positioned to prevent the flow of fluid in conduit 8 from sampling station 28 to the patient, while allowing fluid in conduit 8 from reservoir 2 to be withdrawn from the system at sampling station 28. Lever 20 is held open so that liquid passes from reservoir 2 through conduit 8 at a higher flow rate and is discharged through sampling station 28 into a container (not shown).

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A system for sampling arterial blood from a patient comprising:
a reservoir suitable for containing fluid;
a first conduit having a first end and a second end with the first end connected to said reservoir;
connection means suitable for connection to an artery of a patient and attached to the second end of said first conduit;
a fluid displacement system comprising:
a second conduit having a first end and a second end;
a controller in said second conduit to permit fluid flow through the second conduit; and
a junction where said second conduit connects to said first conduit, wherein the junction is at the first end of the second conduit;
a flow regulator operative in a first mode to convey fluid to a patient through said first conduit from said reservoir and operative in a second mode to remove blood from a patient and convey it in said first conduit to a limit location, positioned between the second end of said first conduit and said junction, wherein removal of blood from the patient in the second mode causes fluid previously in said first conduit to move into said fluid displacement system;
a sampling station in said first conduit positioned between the limit location and the second end of said first conduit; and
a first valve positioned in said first conduit at said sampling station and movable to a first position to permit removal of blood from said first conduit at said sampling station, movable to a second position to permit fluid flow between said reservoir and the patient through said first conduit, and movable to a third position to permit fluid from said reservoir to be removed from said first conduit at said sampling station.

2. A system according to claim 1 further comprising: a receptacle connected to the second end of said second conduit.

3. A system according to claim 1 further comprising:
a lever positioned to allow liquid to flow through said first conduit at either a high flow rate or a low flow rate.

4. A system according to claim 1, further comprising:
a second valve positioned in said first conduit between said reservoir and said junction to control fluid flow from said reservoir through said first conduit.

5. A system according to claim 1, further comprising:
a transducer to measure pressure of fluid in said first conduit and
a calibration station positioned in said first conduit between said reservoir and said junction to calibrate said transducer to atmospheric pressure.

6. A method for sampling arterial blood from a patient utilizing a sampling system comprising:
a reservoir suitable for containing fluid;
a first conduit having a first end and a second end with the first end connected to said reservoir;
connection means suitable to connect the second end of said first conduit to an artery of a patient;

a fluid displacement system comprising:
- a second conduit having a first end and a second end;
- a controller in said second conduit to permit fluid flow through the second conduit; and
- a junction where said second conduit connects to said first conduit, wherein the junction is at the first end of the second conduit;

a flow regulator operative in a first mode to convey fluid to a patient through said first conduit from said reservoir and operative in a second mode to remove blood from a patient and convey it in said first conduit to a limit location, positioned between the second end of said first conduit and said junction, wherein removal of blood from the patient in the second mode causes fluid previously in said first conduit to move into said fluid displacement system;

a sampling station in said first conduit positioned between the limit location and the second end of said first conduit; and a first valve positioned in said first conduit at said sampling station and movable to a first position to permit removal of blood from said first conduit at said sampling station, movable to a second position to permit fluid flow between said reservoir and the patient through said first conduit, and movable to a third position to permit fluid from said reservoir to be removed from said first conduit at said sampling station, said method comprising:

operating said flow regulator system in the second mode to convey blood from the patient through said first conduit to the limit location and to displace fluid previously in said first conduit into said fluid displacement system;

collecting a blood specimen from said sampling station by moving said first valve to the first position;

operating said flow regulator system in the first mode to convey fluid from said reservoir to the patient through said first conduit, thereby reinfusing blood remaining in said first conduit after said collecting into the patient.

7. A method according to claim 6, wherein said sampling system further comprises:

a receptacle connected to the second end of said second conduit.

8. A method according to claim 6 further comprising:

operating said flow regulation system in the first mode to convey fluid from said reservoir to a patient through said first conduit prior to said operating said fluid flow regulator system in the second mode.

9. A method according to claim 6, wherein said first valve is in the second position during said operating said flow regulator system in the second mode and during said operating said flow regulator system in the first mode.

10. A method according to claim 6, wherein said sampling system further comprises:

a lever positioned to allow liquid to flow through said first conduit at either a high flow rate or a low flow rate, wherein said method further comprises:

operating said flow regulator system, said lever, and said first valve in a third mode to flush debris from said first conduit through said sampling station.

11. A method according to claim 10, wherein said first valve is in the third position during said operating said flow regulator system, said lever, and said first valve in a third mode.

12. A method according to claim 6, wherein said sampling system further comprises:

a second valve positioned in said first conduit between said reservoir and said junction to control fluid flow from said reservoir through said first conduit.

13. A method according to claim 6, wherein said sampling system further comprises:

a transducer to measure pressure of fluid in said first conduit and a calibration station positioned in said first conduit between said reservoir and said junction to calibrate said transducer to atmospheric pressure.

14. A method according to claim 6, wherein blood is prevented from passing the limit location during said operating said flow regulator system in the second mode by closing said second conduit with said controller.

* * * * *